United States Patent [19]

Rowsell et al.

[11] 4,296,093

[45] Oct. 20, 1981

[54] CYCLIC CARBOXAMIDES HAVING A PHYSIOLOGICAL COOLING EFFECT

[75] Inventors: David G. Rowsell, Staines; John M. Gascoyne, Southall; Roger Hems, Maidenhead, all of England

[73] Assignee: Wilkinson Sword Limited, London, England

[21] Appl. No.: 118,205

[22] Filed: Feb. 4, 1980

Related U.S. Application Data

[62] Division of Ser. No. 351,356, Apr. 16, 1973, abandoned.

[51] Int. Cl.³ .................. A61K 9/68; A61K 31/16
[52] U.S. Cl. ............................ 424/45; 131/276; 252/522 R; 424/48; 424/54; 424/73; 424/300; 424/305; 424/320; 426/3; 426/534; 426/590; 131/360

[58] Field of Search .............. 424/54, 320, 45, 48

[56] References Cited

U.S. PATENT DOCUMENTS 3,644,653  2/1972  Tcheiltcheff ................ 424/358
4,136,163  1/1979  Watson et al. .............. 424/54

OTHER PUBLICATIONS

Yamasaki et al., Koryo, No. 95 (1970) pp. 39–43.

*Primary Examiner*—Leonard Schenkman
*Attorney, Agent, or Firm*—Leydig, Voit, Osann, Mayer & Holt, Ltd.

[57] ABSTRACT

Compositions are disclosed having a physiological cooling action on the skin. The compositions contain, as the active ingredient, alkyl-substituted cyclohexanamides.

12 Claims, No Drawings

CYCLIC CARBOXAMIDES HAVING A PHYSIOLOGICAL COOLING EFFECT

This is a division of application Ser. No. 351,356, filed Apr. 16, 1973, now abandoned.

This invention relates to ingestible, topical and other compositions having a physiological cooling effect on the skin and on the mucous membranes of the body, particularly the nose, mouth, throat and gastrointestinal tract.

Menthol is well known for its physiological cooling effect on the skin and mucous membranes of the mouth and has been extensively used as a flavouring agent (menthol being a major constituent of oil of peppermint) in foodstuffs, beverages, dentifrices, mouthwashes, etc. and as a component in a wide range of toiletries, liniments and lotions for topical application. Menthol is also a well known tobacco additive for producing a "cool" sensation in the mouth when smoking. Carvomenthol has also been reported as having a physiological cooling effect and so also have N,N-dimethyl-2-ethyl butanamide and N,N-diethyl-2-ethyl butanamide, see French Pat. No. 1,572,332.

It is well established that the "cooling" effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use, in some compositions, it circumscribed by its strong minty odour and its relative volatility.

The present invention is based on the discovery that certain other organic compounds have a physiological cooling effect similar to that obtained with menthol, but do not have the strong minty odour. In many cases the compounds have little or no odour at all. Such compounds therefore find utility as additives in a wide range of ingestible and topical compositions.

The compounds having a physiological cooling effect and utilized in accordance with the present invention are substituted cyclohexanamides of the formula

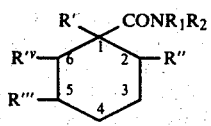

where

R', R'', R''' and R'$^v$ are each hydrogen or $C_1$-$C_5$ alkyl and together provide a total of from 1-8 carbon atoms, it being provided that at least two of R', R'' and R''' and R'$^v$ are hydrogen and that, when R' and R'$^v$ are both hydrogen and R''' is methyl, then R'' is selected from methyl, ethyl, n-propyl and straight and branched chain butyl and amyl;

$R_1$ and $R_2$, when taken separately, each represent hydrogen, $C_1$-$C_5$ alkyl or $C_1$-$C_8$ hydroxyalkyl and together provide a total of no more than 8 carbon atoms with the proviso that when $R_1$ is hydrogen $R_2$ may also be alkylcarboxyalkyl of up to 6 carbon atoms; and $R_1$ and $R_2$, when taken together, represent an alkylene group of up to 6 carbon atoms the ends of which group are attached to the amide nitrogen atom thereby to form a nitrogen heterocycle, the carbon atom chain of which may optionally be interrupted by oxygen.

The preferred cyclohexanamides used in this invention are cyclohexanamides having either one or two nuclear alkyl substituents with the nuclear alkyl substituent in the case of the mono-nuclear substituted compounds being either in the 1- or the 2-position, and in the case of the di-nuclear substituted compounds, the first alkyl substituent being either in the 1- or the 2-position and the second being either in the 5- or the 6-position. Especially preferred are tertiary compounds, i.e. where R' is alkyl. Generally it is preferred that one alkyl group, preferably R', is a branched chain group with branching in an alpha or beta position relative to the ring.

Also preferred are monosubstituted amides, i.e. where one of $R_1$ and $R_2$ is hydrogen, and disubstituted amides where $R_1$ and $R_2$ are methyl or ethyl.

The substituted cyclohexanamides of the above formula exhibit both geometric and optical isomerism and the present invention contemplates using the compounds in an isomerically pure state i.e. consisting of one geometric or optical isomer, as well as in isomer mixtures. In most cases the compounds will be used as an isomer mixture but with certain compounds there may be a difference in cooling effect as between isomers, for example, as between d- and l-forms, and in such cases one or other isomeric form may be preferred.

The amides used in this invention may readily be prepared by conventional techniques, for example, by reaction of an acid chloride of the formula

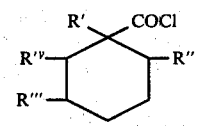

with an amine of the formula $HNR_1R_2$ in the presence of a hydrogen chloride acceptor. Such reactions are entirely conventional and the procedures involved will readily be understood by persons skilled in the art.

Typical amides usable according to the invention are indicated in the following table, together with an indication of their relative activity, i.e. the degree of cooling produced by a given quantity of the compound; the more stars the greater the activity.

TABLE

| R' | R'' | R''' | R'$^v$ | $R_1$ | $R_2$ | Activity |
|---|---|---|---|---|---|---|
| iso-$C_3H_7$— | H | H | H | H | $C_2H_5$— | ***** |
| " | " | " | " | $CH_3$— | $CH_3$— | ***** |
| " | " | " | " | $CH_2$—$CH_2$<br>\|         > <br>$CH_2$—$CH_2$ | | ***** |
| n-$C_3H_7$— | " | " | " | $CH_3$— | $CH_3$— | ***** |
| iso-$C_3H_7$— | $CH_3$— | " | " | H | $C_2H_5$— | ***** |
| sec-$C_4H_9$— | H | " | " | " | " | ***** |

TABLE-continued

| R' | R'' | R''' | R'v | R₁ | R₂ | Activity |
|---|---|---|---|---|---|---|
| iso-$C_4H_9$— | $CH_3$— | " | " | " | " | ***** |
| " | " | " | " | " | $HOCH_2C(CH_3)_2$— | ***** |
| " | " | " | " | $CH_3$— | $CH_3$— | ***** |
| $C_2H_5$— | $C_2H_5$— | " | " | H | $C_2H_5$— | ***** |
| n-$C_3H_7$— | H | " | " | " | n-$C_4H_9$— | **** |
| $C_2H_5$— | $CH_3$— | " | " | " | $C_2H_5$— | **** |
| " | " | " | " | " | $HOCH_2C(CH_3)_2$— | **** |
| " | " | " | " | $CH_3$— | $CH_3$— | **** |
| " | $C_2H_5$— | " | " | H | " | **** |
| H | " | " | " | " | $C_2H_5$— | **** |
| sec-$C_4H_9$— | H | " | " | $CH_3$— | $CH_3$— | **** |
| $CH_3$— | H | " | " | H | $C_2H_5$— | *** |
| n-$C_3H_7$— | " | " | " | " | " | *** |
| " | " | " | " | —$CH_2CH_2OCH_2CH_2$— | | *** |
| H | n-$C_4H_9$— | " | " | H | $C_2H_5$— | *** |
| $C_2H_5$— | $C_2H_5$— | " | " | " | $HOCH_2C(CH_3)_2$— | *** |
| $CH_3$— | H | " | " | " | n-$C_4H_9$— | ** |
| H | $CH_3$— | " | " | " | $C_2H_5$— | ** |
| " | $C_2H_5$— | " | " | " | $C_2H_5OOCCH_2$— | ** |
| " | " | " | " | " | $HOCH_2C(CH_3)_2$— | ** |
| sec-$C_4H_9$— | H | " | " | " | H | ** |
| iso-$C_3H_7$— | " | " | " | " | " | ** |
| n-$C_3H_7$ | " | " | " | " | " | ** |
| H | n-$C_4H_9$— | " | " | " | $C_2H_5OOCCH_2$— | * |
| " | $CH_3$— | $CH_3$— | " | H | $C_2H_5$— | * |
| " | " | " | $CH_3$— | $CH_3$— | $CH_3$— | * |

Certain of the compounds used in accordance with the present invention are novel compounds and as such represent a further aspect of the present invention. The novel compounds are mono- and di-substituted amides of the formula

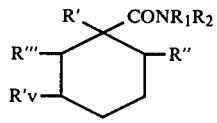

where R', R", R'" and R'$^v$ are as defined above except that, together, they provide a total of from 2-8 carbon atoms, $R_1$ when taken separately is hydrogen, $C_1$-$C_5$ alkyl or $C_1$-$C_8$ hydroxyalkyl, $R_2$ when taken separately, represents $C_1$-$C_5$ alkyl or $C_1$-$C_8$ hydroxyalkyl and together with $R_1$ provides a total of up to 8 carbon atoms, with the proviso that when $R_1$ is hydrogen, $R_2$ may also be alkylcarboxyalkyl of up to 6 carbon atoms; and when taken together $R_1$ and $R_2$ represent an alkylene group of up to 6 carbon atoms, the opposite ends of which group are attached to the amide nitrogen atom to form a nitrogen heterocycle, the carbon atom chain of which may be interrupted by oxygen.

The compounds of the above formulae find utility in a wide variety of compositions for consumption by or application to the human body. Broadly speaking, these compositions can be divided into comestible and topical compositions, both terms being taken in their broadest possible sense. Thus comestible is to be taken as including not only foodstuffs and beverages taken into the mouth and swallowed, but also other orally ingested compositions taken for reasons other than their nutritional value, e.g. indigestion tablets, antacid preparations, laxatives etc. Comestible compositions are also to be taken to include edible compositions taken by mouth, but not necessarily swallowed, eg. chewing gum. Topical compositions are to be taken as including not only compositions such as perfumes, powders and other toiletries, lotions, liniments, oils and ointments applied to the external surfaces of the human body, whether for medical or other reasons, but also compositions applied to, or which, in normal usage, come in contact with, internal mucous membranes of the body, such as those of the nose, mouth, or throat, whether by direct or indirect application or inhalation, and thus include nasal and throat sprays, dentifrice, mouthwash and gargle compositions. Also included within the present invention are toilet articles such as cleansing tissues and toothpicks impregnated or coated with the active cooling compound.

A further class of composition included within the scope of this invention are tobacco and associated articles e.g. pipe and cigarette filters, especially filter tips for cigarettes.

The compositions of this invention will contain an amount of the active cooling compound sufficient to stimulate the cold receptors in the areas of the skin or mucous membrane with which the compositions come into contact and thereby promote the desired cold sensation. As the degree and longevity of cooling sensation varies from compound to compound the quantity of stimulant used in each composition will vary widely. As a guide, it may be said that, with the more active compounds, a significant cooling sensation, which, in some cases, may persist for several hours, is achieved upon application to the skin of as little as 0.05 ml of a 1.0% weight percent solution of the active ingredient in ethanol. For the less active compounds a significant cooling effect is achieved only with more concentrated solutions, e.g. 5% by weight or more of the active ingredient. It must also be admitted that such skin tests are somewhat subjective, some individuals experiencing a greater or lesser cooling sensation than others when subjected to the same test.

In formulating the compositions of this invention the active cooling compound will usually be incorporated into a carrier which may be completely inert or which may be or contain other active ingredients. A wide variety of carriers will be suitable, depending upon the end use of the composition, such carriers including solids, liquids, emulsions, foams and gels. Typical carriers for the active cooling compound include aqueous or alcoholic solutions; oils and fats such as hydrocarbon oils, fatty acid esters, long chain alcohols and silicone oils; finely divided solids such as starch or talc; cellulosic materials such as paper tissue; tobacco; low-boiling hydrocarbons and halohydrocarbons used as aerosol propellants; gums and natural or synthetic resins.

In most compositions according to the invention the carrier will be or contain as an adjuvant one or more of the following: an antacid, antiseptic or analgesic, a flavourant, colourant, or odourant, or a surfactant.

The following illustrate the range of compositions into which the active cooling compounds can be incorporated:

1. Edible or potable compositions including alcoholic and nonalcoholic beverages, confectionery, chewing gum, cachous, ice cream; jellies;

2. Toiletries including after shave lotions, shaving soaps, creams and foams, toilet water, deodorants and antiperspirants, "solid colognes", toilet soaps, bath oils and salts, shampoos, hair oils, talcum powders, face creams, hand creams, sunburn lotions, cleansing tissues, dentifrices, toothpicks, mouthwashes, hair tonics, eye-drops.

3. Medicaments including antiseptic ointments, pile ointments, liniments, lotions, decongestants, counter-irritants, cough mixtures, throat lozenges, antacid and indigestion preparations, oral analgesics;

4. Tobacco preparations including cigars, cigarettes, pipe tobacco, chewing tobacco and snuff; tobacco filters, especially filter tips for cigarettes.

5. Miscellaneous compositions such as water soluble adhesive compositions for envelopes, postage stamps, adhesive labels etc.

Particular preparations according to the invention are discussed in more detail below.

EDIBLE AND POTABLE COMPOSITIONS

The edible and potable compositions of this invention will contain the active cooling compound in combination with an edible carrier and usually a flavouring or colouring agent. The particular effect of the cooling compounds is to create a cool or fresh sensation in the mouth, and in some cases, even in the stomach, and therefore the compounds find particular utility in sugar-based confectionery such as chocolate, boiled sweets and candy, in ice cream and jellies and in chewing gum. The formulation of such confections will be by ordinary techniques and according to conventional recipes and as such forms no part of this invention. The active compound will be added to the recipe at a convenient point and in amount sufficient to produce the desired cooling effect in the final product. As already indicated, the amount will vary depending upon the particular compound, the degree of cooling effect desired and the strength of other flavourants in the recipe. For general guidance, however, amounts in the range 0.1 to 5.0% by weight based on the total composition will be found suitable.

Similar considerations apply to the formulation of beverages. Generally speaking the compound will find most utility in soft drinks e.g. fruit squashes, lemonade, cola etc., but may also be used in alcoholic beverages. The amount of compound used will generally be in the range 0.1 to 2.5% by weight based on the total composition.

TOILETRIES

Because of the cooling sensation imparted to the skin, a major utility of the cooling compound will be in a wide range of toilet preparations and toilet articles. The particular preparations discussed below are to be taken as exemplary.

A major utility will be in after shave lotions, toilet water etc., where the compound will be used in alcoholic or aqueous alcoholic solution, such solutions usually also containing a perfume or mild antiseptic or both. The amount of compound added to the formulation will usually be in the range 0.1 to 10% by weight based on the total composition.

Another field of utility will be in soaps, shampoos, bath oils etc. where the compound will be used in combination with an oil or fat or a natural or synthetic surfactant e.g. a fatty acid salt or a lauroylsulphate salt, the composition usually also containing an essential oil or perfume. The range of soap compositions will include soaps of all kinds e.g. toilet soaps, shaving soaps, shaving foams etc. Usually the compound will be added to the formulation in amount of from 0.1 to 10% by weight.

A further class of toilet compositions into which the compounds may be incorporated includes cosmetic creams and emollients, such creams and emollients usually comprising a base emulsion and optionally a range of ingredients such as wax, preservative, perfume, antiseptics, astringents, pigments etc. Also included within this class are lipstick compositions such compositions usually comprising an oil and wax base into which the compound can be incorporated along with the conventional ingredients i.e. pigments, perfumes etc. Once again the formulation of such compositions, apart from the incorporation of the cooling compound, usually in an amount of from 0.05 to 10% by weight, is conventional.

Compositions for oral hygiene containing the cooling compounds include mouthwash, gargle and dentifrice compositions. The first two may be considered together and will usually comprise an aqueous, alcoholic, or aqueous-alcoholic solution of an antiseptic often coloured or flavoured for palatability, to which the coolant is added in an amount of from 0.1 to 1.0% by weight.

Dentifrice compositions may be of the solid block, powder, paste or liquid type and will usually comprise a finely divided abrasive or polishing material, e.g. precipitated chalk, silica, magnesium silicate, aluminium hydroxide or other similar materials well known in the art, and a detergent or foaming agent. Optional ingredients which may also be included are flavouring agent and colourants, antiseptics, lubricants, thickeners, emulsifiers or plasticizers. The amount of coolant added in such compositions will generally be from 0.1 to 5.0% by weight based on the total composition.

MEDICAMENTS

Because of their cooling effect on the skin and on the mucous membranes of the mouth, throat and nose and of the gastrointestinal tract the cooling compounds may be used in a variety of oral medicines, nasal and throat sprays, and topical compositions, particularly where a counter-irritant is required. In particular the coolants may be formulated into antacid and indigestion remedies, in particular those based on sodium bicarbonate, magnesium oxide, calcium or magnesium carbonate, aluminium or magnesium hydroxide or magnesium trisilicate. In such compositions the coolant will usually be added in an amount of from 0.1 to 2.0% by weight.

The coolants may also be included in oral analgesic compositions e.g. with acetylsalicyclic acid or its salts, and in nasal decongestants e.g. those containing ephedrine.

TOBACCO PREPARATIONS

The coolants of this invention may be incorporated directly into tobacco to give a cool effect when smoking but without the attendant strong and characteristic odour which is associated with mentholated tobacco and cigarettes. Such compositions also have considerable storage stability, which is in contrast with mentholated products. However, a more advantageous utilisation of the coolants of this invention is in pipe or cigarette filters, in particular, filter tipped cigarettes. The pad of filter material, which may be of any of the well known types, e.g. cellulose acetate, paper, cotton α-cellulose or asbestos fiber, is simply impregnated with an alcoholic solution of the coolant and dried to deposit the coolant in the filter pad. The effect is to give a pleasant cool sensation in the mouth when the cigarette is smoked. As little as 0.1 mg. of the coolant is effective.

Compositions of this invention are illustrated by the following Examples.

EXAMPLE I

After Shave Lotion

An after shave lotion was prepared according to the following recipe by dissolution of the ingredients in the liquid and cooling and filtering:

| Denatured Ethanol | 75% |
| --- | --- |
| Diethylphthalate | 1.0% |
| Propylene Glycol | 1.0% |
| Lactic Acid | 1.0% |
| Perfume | 3.0% |
| Water | to 100% |

Into the base lotion was added 1.0% by weight based on the total composition of N-ethyl-2-methyl-1-isopropylcyclohexanamide.

When the final lotion is applied to the face a clearly noticeable cooling effect becomes apparent after a short interval of time.

EXAMPLE II

Eye Lotion

An eye lotion was prepared containing the following ingredients:

| Witch Hazel | 12.95% |
| --- | --- |
| Boric Acid | 2.00% |
| Sodium Borate | 0.50% |
| Allantoin | 0.05% |
| Salicylic Acid | 0.025% |
| Chlorobutol | 0.02% |
| Zinc Sulphate | 0.004% |
| Water | to 100% |

To the formulation was added 0.01%, based on the total composition, of N,2-diethylcyclohexanamide. When used to bathe the eyes a cool fresh sensation is apparent on the eyeball and eyelids.

EXAMPLE III

Toothpaste

The following ingredients were mixed in a blender:

| Dicalcium Phosphate | 48.0% |
| --- | --- |
| Sodium lauryl sulphate | 2.5% |
| Glycerol | 24.8% |
| Sodium carboxymethyl cellulose | 2.0% |
| Citrus flavourant | 1.0% |
| Sodium saccharin | 0.5% |
| Water | to 100% |

Shortly before completion of the bleaching operation 1% by weight of N,N-dimethyl-1-isopropylcyclohexanamide was added to the blender.

When applied as a toothpaste, a cooling effect is noticed in the mouth.

EXAMPLE IV

Soft Sweet

Water was added to icing sugar at 40° C. to form a stiff paste. 0.5% of N-ethyl-1-n-propylcyclohexanamide was then stirred into the paste and the mixture allowed to set. A soft sweet mass resulted having the characteristic cooling effect in the mouth of peppermint but without the minty flavour or odour.

EXAMPLE V

Cigarette Tobacco

A proprietary brand of cigarette tobacco was impregnated with N-ethyl-1-isopropylcyclohexanamide and was rolled into cigarettes each containing approximately 0.001 gm. of active compound. Smoking the impregnated cigarettes produced a cool effect in the mouth characteristic of mentholated cigarettes but without any attendant odour other than than normally associated with tobacco.

A similar effect is noticed when smoking a proprietary brand of tipped cigarette, the coolant being used to impregnate the filter tip rather than the tobacco.

EXAMPLE VI

Antiseptic Ointment

An ointment was prepared according to the following formulation:

| Cetyltrimethyl ammonium bromide | 4.0% |
| --- | --- |
| Cetyl Alcohol | 6.0% |
| Stearyl Alcohol | 6.0% |
| White Paraffin | 14.0% |
| Mineral Oil | 21.0% |
| Water | to 100% |

The ingredients were mixed, warmed to 40° C. and emulsified in a high speed blender. Added to the mixture during blending was 3.0% N-(1,1-dimethyl-2-hydroxyethyl)-1-isobutyl-2-methylcyclohexanamide.

The final ointment when applied to the skin gave rise to a marked cooling effect.

EXAMPLE VII

Aerosol Shaving Soap

An aerosol shaving soap composition was formulated according to the following recipe:

| Stearic acid | 6.3% |
| --- | --- |
| Lauric acid | 2.7% |
| Triethanolamine | 4.6% |
| Sodium carboxymethyl cellulose | 0.1% |

| | |
|---|---|
| Sorbitol | 5.0% |
| Perfume | 0.4% |
| Water | to 100% |

The composition was prepared by fusing the acids in water, adding the triethanolamine, cooling and adding the other constituents. To the mixture was then added 2.0%, based on the total composition of N,2-diethyl cyclohexanamide. The composition was then packaged in an aerosol dispenser under pressure of a butane propellent.

When used in shaving a fresh cool sensation was distinctly noticeable on the face.

EXAMPLE VIII

Toilet Water

A toilet water was prepared according to the following recipe:

| | |
|---|---|
| Denatured ethanol | 75.0% |
| Perfume | 5.0% |
| Water | to 100% |

To the recipe was added 3.0% based on the total composition, of N,N,2-trimethyl-1-isobutylcyclohexanamide.

As with the after shave lotion, a cooling effect was clearly noticeable on the skin well after the termination of any cooling effect attributable to the evaporation of the alcoholic carrier.

EXAMPLE IX

Deodorant Composition

A deodorant composition suitable for formulation and dispensing as an aerosol under pressure of a suitable propellent was formulated according to the following recipe:

| | |
|---|---|
| Denatured ethanol | 96.9% |
| Hexachlorophene | 2.0% |
| Isopropyl myristate | 1.0% |
| Perfume | 0.1% |

To the composition was added 2.5% by weight of N-(2-hydroxy-1,1-dimethyl-ethyl)-1-ethyl-2-methyl cyclohexanamide. Application of the final composition gave rise to a definite cooling sensation on the skin.

EXAMPLE X

Hair Shampoo

Sodium lauryl ether sulphate, 10 g, was dispersed in 90 g. water in a high speed mill. To the dispersion was added 3.0% by weight of N-methyl-1,2-diethyl cyclohexanamide. When the hair is washed using the shampoo a fresh, cool sensation is noticed on the scalp.

EXAMPLE XI

Solid Cologne

A solid cologne was formulated according to the following recipe:

| | |
|---|---|
| Denatured ethanol | 74.5% |
| Propylene glycol | 3.0% |
| Sodium stearate | 5.0% |
| Perfume | 5.0% |
| Water | to 100% |

The sodium stearate was dissolved by stirring in a warm mixture of the ethanol, propylene glycol and water. To the solution was added the perfume and 2.0% of N-ethyl-1-sec.butyl cyclohexanamide and the mixture then allowed to solidify into a waxy cake.

When applied to the forehead a distinct cooling effect is noticeable

EXAMPLE XII

Mouthwash

A concentrated mouthwash composition was prepared according to the following recipe:

| | |
|---|---|
| Ethanol | 3.0% |
| Borax | 2.0% |
| Sodium bicarbonate | 1.0% |
| Glycerol | 10.0% |
| Flavourant | 0.4% |
| Thymol | 0.03% |
| Water | to 100% |

To the composition was added 0.1% of N-ethyl-1-isopropyl-2-methyl cyclohexanamide.

When diluted with approximately 10 times its own volume of water and used to rinse the mouth a cooling effect is obtained in the mouth.

EXAMPLE XIII

Toothpicks

The tip of a wooden toothpick was impregnated with an alcoholic solution containing N-ethyl-1-methylcyclohexanamide in sufficient amount to deposit on the toothpick 0.10 mg. of the compound. The impregnated toothpick was then dried. When placed on the tongue there is no detectable taste, however, a distinct cooling effect is noticeable after a short period of time.

EXAMPLE XIV

Soft Drink

A soft drink concentrate was prepared from the following recipe:

| | |
|---|---|
| Pure orange juice | 60% |
| Sucrose | 10% |
| Saccharin | 0.2% |
| Orange flavouring | 0.1% |
| Citric acid | 0.2% |
| Sulphur dioxide | trace amount |
| Water | to 100% |

To the concentrate was added 0.10% of N-n-butyl-1-n-propyl cyclohexanamide.

The concentrate was diluted with water and tasted. An orange flavour having a pleasantly cool after-effect was obtained.

EXAMPLE XV

Boiled Sweet 99.5% sucrose and 0.5% citric acid were carefully fused together in the presence of a trace of water. Just before casting the melt onto a chilled plate 0.5% of N-ethyl-1-isopropyl cyclohexanamide was rapidly stirred in. The melt was then cast. A boiled sweet resulted having a marked cooling effect on the mouth.

EXAMPLE XVI

Indigestion tablet

The following ingredients were ground together:

| | |
|---|---|
| Magnesium carbonate | 49.5% |
| Sorbitol | 49.4% |
| Saccharin | 0.1% |
| Talc | 1.0% |

Added to the mixture during grinding was 0.10% of N,N,2-trimethyl-1-ethylcyclohexanamide. After mixing the mixture was pressed into 0.5 g. tablets.

Taken by mouth and swallowed the tablets produced after a short interval of time a noticeable cooling effect in the stomach.

EXAMPLE XVII

Cleansing Tissue

A cleansing liquid was prepared having the formulation:

| | |
|---|---|
| Triethanolamine Lauryl Sulphate | 1.0% |
| Glycerol | 2.0% |
| Perfume | .95% |
| Water | to 100% |

To this liquid was added 2.0% of N,1,2-triethyl cyclohexanamide. A paper tissue was then soaked in the liquid.

When the impregnated tissue was used to wipe the skin a fresh cool sensation developed on the skin after a short interval.

The above Examples illustrate the range of compounds and the range of compositions included within the present invention. However, they are not to be taken as limiting the scope of the invention in any way. Other compounds within the general formula will be equally suitable for use in the compositions of Examples I–XVII and the physiological cooling effect obtained with the compounds of the invention will recommend their use in a wide variety of other compositions where the cooling effect will be of value.

The novel compounds of this invention are illustrated by the following Examples. All temperatures are given in degrees Centigrade. The cyclohexanecarboxylic acids used as starting materials were prepared either by carbonation of Grignard reagents or by hydrolysis of alkylcyclohexyl cyanides according to known techniques.

EXAMPLE XVIII

Preparation of N-Ethyl-1-Isopropylcyclohexanamide 1-isopropylcyclohexanoyl chloride was prepared from 1-isopropylcyclohexanoic acid and thionyl chloride. A solution of this acid chloride (2.6 g) in ether (25 ml) was added dropwise to a stirred solution of ethylamine (5 ml of a 70% solution in water) in ether (100 ml). After 2 hours the ethereal solution was washed with dilute hydrochloric acid and water, dried (MgSO$_4$) and concentrated to give a white solid. This was recrystallised from petroleum ether (bp. 40°–60°) to give N-ethyl-1-isopropylcyclohexanamide, mp. 101°–2°.

Analysis: Found: C: 73.5; H: 11.9; N: 7.2. Calculated: C: 73.2; H: 11.7; N: 7.1%.

EXAMPLE XIX

Preparation of N-n-Butyl-1-n-Propylcyclohexanamide 1-n-propylcyclohexanoyl chloride (bp. 118°–122°/16 mm) was prepared in the usual way from 1-n-propylcyclohexanoic acid and thionyl chloride. A solution of this acid chloride (2.0 g) in ether (20 ml) was added dropwise to a stirred solution of n-butylamine (3.0 g) in ether (100 ml). After 3 hours the ethereal solution was washed with dilute hydrochloric acid and water, dried (MgSO$_4$), and concentrated to give a colourless syrup. Distillation gave N-n-butyl-1-n-propylcyclohexanamide, bp. 116°–8°/1 mm.

Analysis: Found: C: 74.8; H: 12.1; N: 6.3. Calculated: C: 74.7; H: 12.0; N: 6.2%.

EXAMPLE XX

Preparation of N,N-Dimethyl-1-n-Propylcyclohexanamide

The procedure of Example XIX was repeated but using dimethylamine in place of n-butylamine, N,N-dimethyl-1-n-propylcyclohexanamide was obtained as a colourless liquid, bp. 63°–66°/0.01 mm.

Analysis: Found: C: 73.7; H: 11.7; N: 7.3. Calculated: C: 73.0; H: 11.7; N: 7.1%.

EXAMPLE XXI

Preparation of N-(1-n-Propylcyclohexanoyl)Morpholine

The procedure of Example XIX was repeated but using morpholine in place of n-butylamine. N-(1-n-propylcyclohexanoyl)morpholine was obtained as a colourless syrup, bp. 105°–114°/0.01 mm.

Analysis: Found: C: 70.1; H: 10.9; N: 5.7. Calculated: C: 70.5; H: 10.5; N: 5.9%.

EXAMPLE XXII

Preparation of N-(1,1-Dimethyl-2-Hydroxyethyl)-1-Ethyl-2-Methylcyclohexanamide 1-ethyl-2-methylcyclohexanoyl chloride (bp. 108°–114°/15 mm) was prepared in the usual way. A solution of this acid chloride (1.0 g) in ether (20 ml) was added to a stirred solution of 2-amino-2-methylpropan-1-ol (1.0 g) in ether (100 ml). After 17 hours the product was isolated as in Example XVIII. Distillation gave N-(1,1-dimethyl-2-hydroxyethyl)-1-ethyl-2-methylcyclohexanamide, bp. 136°–143°/1.0 mm, as a colourless liquid which slowly solidified.

Analysis: Found: C: 69.1; H: 11.3; N: 5.7. Calculated: C: 69.7; H: 11.2; N: 5.8%.

EXAMPLE XXIII

Preparation of N,N,2-Trimethyl-1-Isobutylcyclohexanamide 1-isobutyl-2-methylcyclohexanoyl chloride (bp. 124°–126.5°/10 mm) was prepared in the usual way. A solution of this acid chloride in ether was treated with dimethylamine as in Example XX. After work up, distillation of the residue gave N,N,2-trimethyl-1-isobutylcyclohexanamide, bp. 103°–107°/0.9 mm.

Analysis: Found: C: 74.0; H: 12.2; N: 6.3. Calculated: C: 74.6; H: 12.0; N: 6.2%.

EXAMPLE XXIV

Preparation of N-2-Diethylcyclohexanamide 2-ethylcyclohexanoyl chloride was prepared in the usual way. The acid chloride was allowed to react with an excess of ethylamine in ether solution and the product was worked up as in Example XVIII to give N,2-diethylcyclohexanamide as a colourless liquid, bp. 84°–94°/0.01 mm.

We claim:

1. In a manufactured consumer product for application to or consumption by the human body and being:
   (a) a personal care product comprising a topically or orally administrable base medium containing a flavourant, colourant, perfume, surface active agent or antiseptic agent;
   (b) an ingestible preparation comprising an edible or potable base containing a flavourant or colourant.
   (c) a pharmaceutical preparation comprising a topically or orally administrable pharmaceutically acceptable carrier and an active pharmaceutical ingredient; or
   (d) a tobacco containing consumer product, said consumer product also containing an ingredient capable of stimulating the cold receptors of the nervous system of the surface tissues of the body when brought into contact therewith by application or consumption of the said product, the improvement which comprises using as said cold receptor stimulating ingredient an effective amount of a cyclic carboxamide of the formula

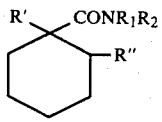

wherein
R′ is $C_1$–$C_5$ alkyl and R″ is hydrogen or $C_1$–$C_5$ alkyl, with the proviso that R′ and R″ together provide a total of from 1–8 carbon atoms; and
$R_1$ and $R_2$ are each hydrogen, $C_1$–$C_5$ alkyl or $C_1$–$C_8$ hydroxyalkyl and together provide a total of 0 to 8 carbon atoms, with the proviso that when $R_1$ is H then $R_2$ may also be alkylcarboxyalkyl of up to 6 carbon atoms.

2. A product according to claim 1, wherein R′ is a $C_3$–$C_5$ branched chain alkyl group with branching in an alpha or beta position relative to the ring.

3. A product according to claim 1, wherein R″ is hydrogen, methyl or ethyl.

4. A product according to claim 1, which is a toilet or cosmetic lotion comprising an aqueous, alcoholic or aqueous alcoholic carrier, an antiseptic or odourant, and an effective amount of said cold receptor stimulating compound.

5. A product according to claim 1, which is a toilet or cosmetic lotion or cream comprising an oleaginous carrier, an antiseptic or odourant, and an effective amount of said cold receptor stimulating compound.

6. A product according to claim 1, which is a shaving foam preparation comprising a foamable base, a surfactant, an odourant, or antiseptic and an effective amount of said cold receptor stimulating compound.

7. A product according to claim 1, which is a dentifrice comprising an effective amount of said cold receptor stimulating compound.

8. A product according to claim 1, which is a mouthwash comprising an aqueous or aqueous-alcoholic carrier, an antiseptic, and an effective amount of said cold receptor stimulating compound.

9. A product according to claim 1, which is a chewing gum, comprising an edible chewing gum base, a flavourant and an effective amount of a cold receptor stimulating cyclic carboxamide of the formula defined in claim 1.

10. A product according to claim 1, which is a cigarette containing an effective amount of said cold receptor stimulating compound.

11. A product according to claim 1, which is a filter tip cigarette containing an effective amount of said cold receptor stimulating compound impregnated in the filter tip.

12. A method of stimulating the cold receptors of the nervous system in the surface tissues of the human body which comprises contacting said receptors with an effective amount of a cold receptor stimulating compound of the formula defined in claim 1.

* * * * *